(12) United States Patent
Liu (10) Patent No.: US 9,662,075 B2
(45) Date of Patent: May 30, 2017

(54) METHOD AND APPARATUS FOR CONTROLLING SCANNING PREPARATION

(71) Applicant: Shenyang Neusoft Medical Systems Co., Ltd., Shenyang (CN)

(72) Inventor: Jinjun Liu, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 353 days.

(21) Appl. No.: 14/569,787

(22) Filed: Dec. 15, 2014

(65) Prior Publication Data
US 2015/0164460 A1 Jun. 18, 2015

(30) Foreign Application Priority Data
Dec. 18, 2013 (CN) .......................... 2013 1 0714921

(51) Int. Cl.
*A61B 6/00* (2006.01)
*A61B 6/03* (2006.01)

(52) U.S. Cl.
CPC ................. *A61B 6/032* (2013.01); *A61B 6/54* (2013.01); *A61B 6/467* (2013.01); *A61B 6/547* (2013.01)

(58) Field of Classification Search
CPC ..... A61B 6/032; A61B 6/5205; A61B 6/5258; A61B 6/4085; A61B 6/488; A61B 6/5217; A61B 6/06; G01N 23/046; G01N 23/04
See application file for complete search history.

(56) References Cited

U.S. PATENT DOCUMENTS

| 2003/0095144 A1 | 5/2003 | Trevino et al. |
| 2007/0189445 A1 | 8/2007 | Haras et al. |
| 2009/0016484 A1* | 1/2009 | Wang ..................... A61B 6/032 378/19 |
| 2010/0183206 A1 | 7/2010 | Carlsen et al. |

(Continued)

FOREIGN PATENT DOCUMENTS

| CN | 101686825 A | 3/2010 |
| CN | 101977549 A | 2/2011 |

(Continued)

OTHER PUBLICATIONS

The first Office Action issued on Jun. 24, 2015, 2015 regarding the Chinese priority patent application (201310714921.X).

*Primary Examiner* — Hoon Song
(74) *Attorney, Agent, or Firm* — Kilpatrick Townsend & Stockton LLP (57) ABSTRACT

A method for controlling scanning preparation includes: obtaining a first scanning protocol of a current CT examination, controlling a CT scanner to perform a scanning preparation for a first scanning series according to the first scanning protocol; in case that there are one or more subsequent scanning series, controlling CT scanner to perform scanning preparations for the subsequent scanning series according to the first scanning protocol, where for each subsequent scanning series, the scanning preparation is performed during time interval between end of exposure of scanning series previous to the subsequent scanning series and starting of the subsequent scanning series; and obtaining a second scanning protocol of next CT examination and controlling the CT scanner to perform a scanning preparation for a first scanning series according to the second scanning protocol.

20 Claims, 2 Drawing Sheets

--- obtaining a first scanning protocol of a current CT examination, and controlling a CT scanner to perform a scanning preparation for a first scanning series according to the first scanning protocol — 101

↓ in a case that there are one or more subsequent scanning series after the first scanning series, controlling the CT scanner to perform scanning preparations for the subsequent scanning series according to the first scanning protocol in sequence, where for each of the subsequent scanning series, the scanning preparation for the subsequent scanning series is performed during a time interval between an end of exposure of a scanning series previous to the subsequent scanning series and a starting of the subsequent scanning series — 102

↓ after completion of a last scanning series, obtaining a second scanning protocol of a next CT examination, and controlling the CT scanner to perform a scanning preparation for a first scanning series according to the second scanning protocol — 103

(56) References Cited

U.S. PATENT DOCUMENTS

| | | | |
|---|---|---|---|
| 2010/0274118 A1 | 10/2010 | Arnold et al. | |
| 2011/0021904 A1 | 1/2011 | Burrman | |
| 2012/0093383 A1* | 4/2012 | Claus | A61B 6/032 |
| | | | 382/131 |
| 2012/0213326 A1* | 8/2012 | Walker | A61B 6/032 |
| | | | 378/4 |

FOREIGN PATENT DOCUMENTS

| | | |
|---|---|---|
| CN | 102576387 A | 7/2012 |
| JP | 2007190392 A | 8/2007 |
| WO | 2012052901 A1 | 4/2012 |

\* cited by examiner

METHOD AND APPARATUS FOR CONTROLLING SCANNING PREPARATION

This application claims priority to Chinese Patent Application No. 201310714921.X, entitled "METHOD AND APPARATUS FOR CONTROLLING SCANNING PREPARATION", filed with the Chinese State Intellectual Property Office on Dec. 18, 2013, which is incorporated by reference in its entirety herein.

FIELD

The present application relates to the field of medical technology, particularly to a method and an apparatus for controlling a scanning preparation.

BACKGROUND

As increasing of rotation speed of a scanner gantry of a Computed Tomography (CT) scanner, increasing of rows of detectors, increasing of capacity of an X-ray tube, and adopting of low dose scanning technology, under a premise of a lowered level of x-ray irradiated on an object to be scanned (a patient), quality of images of the object obtained by CT scanning remains unchanged or is even improved. A process of a CT examination usually includes positioning and registration of an object to be scanned, and one or more series of scanning. The series scanning may be a surview scanning, an axial scanning or a helical scanning.

In view of the above improvement of the CT-related technology, a CT scanning can be completed within one respiratory cycle currently. However, the process such as positioning and registration of an object and scanning preparation for each scanning series often takes a longer time than one respiratory cycle. In the conventional CT scanning process, CT scanning preparation is performed after the positioning and registration of the object, and various scanning processes are independent with each other, i.e., one series of scanning is not associated with the next series of scanning or the scanning of the next object, therefore, it takes a long time for the CT scanning process.

SUMMARY

In view of the above, a method and an apparatus for controlling a scanning preparation are provided by embodiments of the application, to shorten total time for scanning examinations.

To achieve the purpose above, a method for controlling a scanning preparation is provided by an embodiment of the application, including: obtaining a first scanning protocol of a current CT examination, and controlling a CT scanner to perform a scanning preparation for a first scanning series according to the first scanning protocol; in a case that there are one or more subsequent scanning series after the first scanning series, controlling the CT scanner to perform scanning preparations for the subsequent scanning series according to the first scanning protocol in sequence, where for each of the subsequent scanning series, the scanning preparation for the subsequent scanning series is performed during a time interval between an end of exposure of a scanning series previous to the subsequent scanning series and a starting of the subsequent scanning series; and after completion of a last scanning series, obtaining a second scanning protocol of a next CT examination, and controlling the CT scanner to perform a scanning preparation for a first scanning series according to the second scanning protocol.

An apparatus for controlling a scanning preparation is further provided by an embodiment of the application, including: a first scanning preparation control module, configured to obtain a first scanning protocol of a current CT examination, and control a CT scanner to perform a scanning preparation for a first scanning series according to the first scanning protocol; a second scanning preparation control module, configured to, in a case that there are one or more subsequent scanning series after the first scanning series, control the CT scanner to perform scanning preparations for the subsequent scanning series according to the first scanning protocol in sequence, where for each of the subsequent scanning series, the scanning preparation for the subsequent scanning series is performed during a time interval between an end of exposure of a scanning series previous to the subsequent scanning series and a starting of the subsequent scanning series; and a third scanning preparation control module, configured to, after completion of a last scanning series, obtain a second scanning protocol of a next CT examination, and control the CT scanner to perform a scanning preparation for a first scanning series according to the second scanning protocol.

With the method and the apparatus for controlling the scanning preparation of the application, after the first scanning protocol of the current CT examination is obtained, the CT scanner is controlled to perform a scanning preparation for the first scanning series according to the first scanning protocol, instead of performing the scanning preparation after positioning and registration of the object to be scanned as in the conventional technology, therefore, the time for the scanning examination is reduced. Furthermore, for subsequent scanning series, the scanning preparation for the scanning series is performed immediately after completion of exposure of a previous scanning series, therefore, the time for the scanning examination is further reduced. Furthermore, after the last scanning series is completed, a scanning preparation for a first scanning series of a next CT examination is immediately performed, therefore, a time interval between two scanning examinations is made use of and the time for the scanning examination is further reduced.

BRIEF DESCRIPTION OF THE DRAWINGS

To better explain technical solutions in embodiments of the present application or in conventional technology, the drawings for the embodiments of the application and for the conventional technology are described briefly below. Apparently, the drawings described below are merely a few embodiments of the application. Other drawings may be obtained by those skilled in the art based on these drawings without any creative work.

DETAILED DESCRIPTION

To make purposes, technical solutions and advantages of embodiments of the present application clearer, technical solutions of the application are described in detail below in combination with the drawings in the embodiments in the application. Apparently, the described embodiments are not all, but merely a few embodiments of the application. Based on these embodiments, all other embodiments obtained by those skilled in the art without paying creative work are within the scope of the application.

Figure 1:
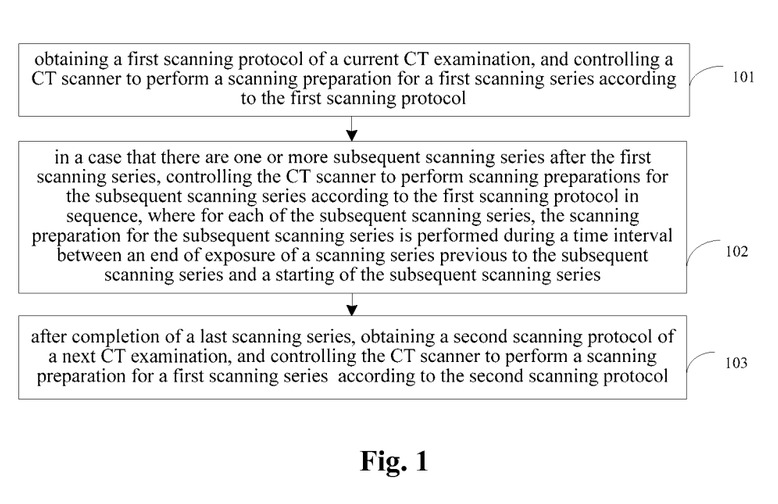
FIG. 1 is a flow chart of a method for controlling a scanning preparation according to an embodiment of the application.

FIG. 1 is a flow chart of a method for controlling a scanning preparation according to an embodiment of the application, including steps 101-103.

In step 101, a first scanning protocol corresponding to a current CT examination is obtained, and a CT scanner is controlled to perform a scanning preparation for a first scanning series according to the first scanning protocol.

Two implementations are provided for step 101.

The first implementation is described as follows.

For a first scanning series of a CT examination, an object to be scanned may be registered firstly, and then the object is positioned. An apparatus for controlling a scanning preparation obtains a first scanning protocol corresponding to the current CT examination before the completion of the positioning of the object. The first scanning protocol is generated based on registration information of the object to be scanned. The apparatus for controlling the scanning preparation then controls a CT scanner to perform a scanning preparation for a first scanning series according to the first scanning protocol. In this way, an automatic scanning preparation for the first scanning series is completed during the positioning of the object. Therefore, a condition in the conventional scanning process that the scanning preparation for the first scanning series is performed after completion of the registration and positioning is avoid, and the time for a scanning examination is reduced. The first scanning protocol indicates a scanning mode of the first scanning series (a surview scan, an axial scan or a helical scan).

For the registration of the object to be scanned, a doctor may obtain information of the object to be scanned directly from the object, or may obtain information of the object to be scanned via an information system such as Picture Archiving and Communication Systems (PACS). The doctor may select a set of scanning protocols suitable for the object to be scanned after obtaining the information of the object. The apparatus for controlling the scanning preparation starts a scanning preparation for the first scanning series after obtaining the scanning protocol. Since the process of the scanning preparation is performed automatically after the scanning protocol is obtained, the scanning preparation for the first scanning series is substantially completed during the positioning of the object to be scanned.

Figure 2:
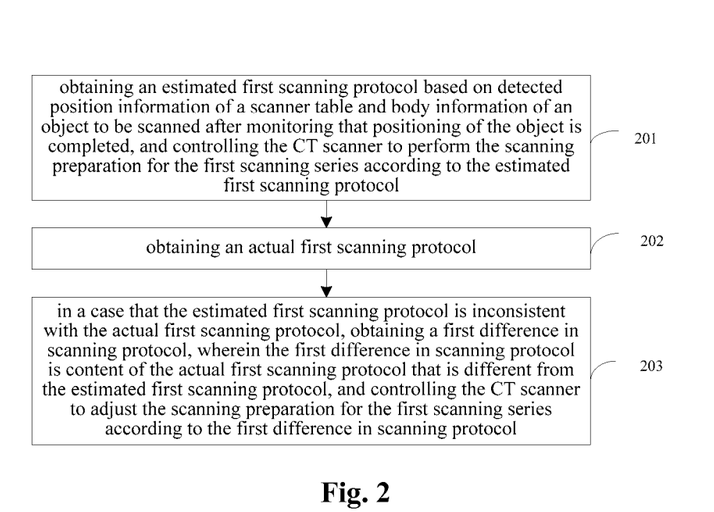
FIG. 2 is a flow chart of a method for controlling a scanning preparation for a first scanning series according to an embodiment of the application.

The second implementation is described as follows.

FIG. 2 is a flow chart of a method for controlling a scanning preparation for the first scanning series, including steps 201-203.

In step 201, after the positioning of the object to be scanned is completed, an estimated first scanning protocol is obtained based on detected position information of a scanner table and body information of the object to be scanned, and the CT scanner is controlled to perform a scanning preparation for the first scanning series according to the estimated first scanning protocol.

For a first scanning series of a CT scanning examination, the object to be scanned may be positioned firstly, and then the object to be scanned is registered. During the positioning the object, a sensing device of a scanner table for the object to be scanned and a sensing device for sensing closing of a door of a CT room may be adopted to detect whether the positioning of the object is completed. Specifically, in a case that the weight placed on the scanner table is changed and the door of the CT room is in a closed state in a preset time, it can be determined that the positioning of the object to be scanned is completed.

After the positioning is completed, the apparatus for controlling the scanning preparation may detect position information of the scanner table and body information of the object to be scanned. The position information of the scanner table includes, for example, height of the scanner table and an inclination angle of the scanner table. The body information includes, for example, height and weight of the object to be scanned. The apparatus for controlling the scanning preparation then obtains an estimated first scanning protocol based on the detected position information of the scanner table and body information of the object to be scanned. The first scanning protocol indicates the scanning mode of the first scanning series (a surview scan, an axial scan or a helical scan), and the scanning modes of the subsequent scanning series.

In step 202, an actual first scanning protocol is obtained.

In performing step 201, a doctor registers information of the object to be scanned and selects a scanning protocol suitable for the object to be scanned based on the registration information. The selected scanning protocol is the actual first scanning protocol to be performed. The apparatus for controlling the scanning preparation may obtain the actual first scanning protocol input by the doctor.

In step 203, in a case that the estimated first scanning protocol is inconsistent with the actual first scanning protocol, a first difference in scanning protocol is obtained. The first difference in scanning protocol is a different content between the actual first scanning protocol and the estimated first scanning protocol. The CT scanner is then controlled to adjust the scanning preparation for the first scanning series according to the first difference in scanning protocol.

Since the estimated first scanning protocol may be partially inconsistent with the actual first scanning protocol, the apparatus for controlling the scanning preparation extracts the different content (the content of the actual first scanning protocol which is different from the estimated first scanning protocol), and partially adjusts, according to the extracted different content of the scanning protocol, the scanning preparation performed according to the estimated first scanning protocol in step 201.

For implementation of step 201, a database with various pieces of first preset information is established in advance. The first preset information includes position information of a scanner table and body information of an object to be scanned. Scanning protocols corresponding to the various pieces of the first preset information are also preset in the database. The position information of the scanner table includes, for example, height of the scanner table and an inclination angle of the scanner table. The body information includes, for example, height and weight of the object to be scanned.

The process of obtaining the estimated first scanning protocol based on the detected position information of the scanner table and body information of the object to be scanned in step 201 may be implemented based on the established database as follows: querying the database for the first preset information corresponding to the detected position information of the scanner table and body information of the object to be scanned, and obtaining from the database the first scanning protocol corresponding to the obtained first preset information.

It is to be noted that the various pieces of the first preset information and the corresponding scanning protocols in the database may be preset according to statistical data of hospitals. The database also has a self-learning function, that is, the database may be updated in a real time manner based on data obtained in actual scanning preparations. The first difference in scanning protocol obtained in step 203 may be used to update the first scanning protocol corresponding to the obtained first preset information in the database.

In step 102, in a case that there are one or more subsequent scanning series after the first scanning series, the CT scanner is controlled to perform scanning preparations for the subsequent scanning series according to the first scanning protocol in sequence, where for each of the subsequent scanning series, the scanning preparation for the subsequent scanning series is performed during a time interval between an end of exposure of a scanning series previous to the subsequent scanning series and a starting of the subsequent scanning series.

In step 103, after the completion of the last scanning series, a second scanning protocol corresponding to a next CT examination is obtained, and the CT scanner is controlled to perform a scanning preparation for a first scanning series according to the second scanning protocol.

After the last scanning series of the current CT examination, the apparatus for controlling the scanning preparation may perform a preparation for the next CT examination. For example, the CT scanner may be controlled to perform a scanning preparation for a first scanning series of the next CT examination according to the second scanning protocol during a time interval between the completion of the last scanning series of the current CT examination and a starting of the first scanning series of the next CT examination. After the completion of the last scanning series, the apparatus for controlling the scanning preparation may perform a scanning preparation for the first scanning series according to a scanning protocol prepared for an object reserved to be scanned or a next object waited to be scanned. The scanning protocol prepared for the object reserved to be scanned or the next object waited to be scanned is prepared based on registration information of the object. The registration information of the object reserved to be scanned may be obtained in advance by an information system such as PACS or by a telephone booking. The registration information of the next object waited to be scanned may be obtained by on-site registration. The second scanning protocol for the next scanning examination is required to be input in advance, so that the apparatus for controlling the scanning preparation controls the CT scanner to perform the scanning preparation for the first scanning series according to the second scanning protocol immediately after the completion of the last scanning series of current CT examination.

Figure 3:
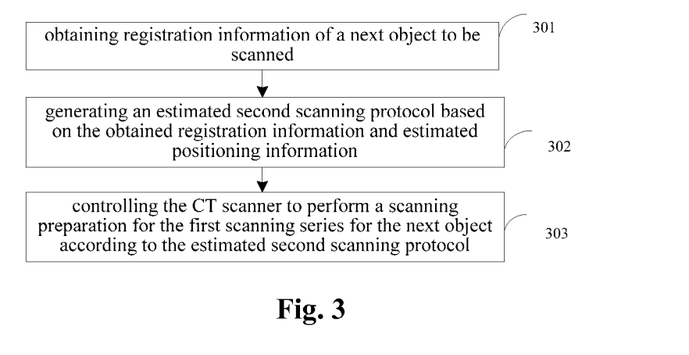
FIG. 3 is a flow chart of a method for controlling a scanning preparation for a first scanning series according to an embodiment of the application.

Based on the above, obtaining the second scanning protocol corresponding to the next CT examination and controlling the CT scanner to perform the scanning preparation for the first scanning series according to the second scanning protocol in step 103 may be implemented as follows. FIG. 3 illustrates a flow chart of a method for controlling a scanning preparation for a first scanning series, including steps 301-303.

In step 301, registration information of the next object to be scanned is obtained.

The next object to be scanned may be an object reserved to be scanned or a next object waited to be scanned.

In step 302, an estimated second scanning protocol is generated based on the obtained registration information and estimated positioning information.

For implementation of step 302, various pieces of second preset information may be pre-stored in the database. The second preset information includes registration information and positioning information of an object to be scanned. Scanning protocols corresponding to the various pieces of the second preset information may also be preset in the database. Therefore, step 302 may be implemented as follows: querying the database for the second preset information corresponding to the obtained registration information and the estimated positioning information, and obtaining from the database the second scanning protocol corresponding to the obtained second preset information.

In step 303, the CT scanner is controlled to perform a scanning preparation for the first scanning series according to the estimated second scanning protocol.

For the next CT examination, a doctor selects an actual second scanning protocol suitable for the object to be scanned according to actual conditions of the object to be scanned. After obtaining the actual second scanning protocol, the apparatus for controlling the scanning preparation determines whether the actual second scanning protocol is consistent with the estimated second scanning protocol. In a case that the actual second scanning protocol is inconsistent with the estimated second scanning protocol, the apparatus for controlling the scanning preparation extracts a different content in scanning protocol (the content of the actual second scanning protocol which is different from the estimated second scanning protocol), and partially adjusts, according to the extracted content of the scanning protocol, the scanning preparation performed according to the estimated second scanning protocol in step 303. Based on the above, following steps may be further performed after step 303: obtaining an actual second scanning protocol; and in a case that the estimated second scanning protocol is inconsistent with the actual second scanning protocol, obtaining a second difference in scanning protocol, where the second difference in scanning protocol is the content of the actual second scanning protocol which is different from the estimated second scanning protocol, and controlling the CT scanner to adjust the scanning preparation for the first scanning series according to the second difference in scanning protocol.

It is to be noted that the various pieces of the second preset information and the corresponding scanning protocols in the database may be preset according to statistical data of hospitals. The database also has a self-learning function, that is, the database may be updated in a real time manner based on data obtained in actual scanning preparations. The obtained second difference in scanning protocol may be used to update the second scanning protocol corresponding to the obtained second preset information in the database.

Figure 4:
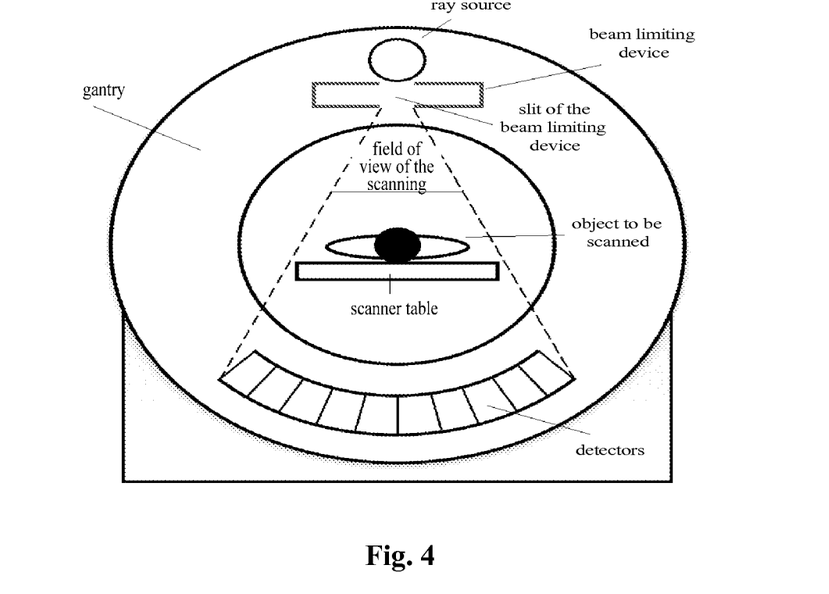
FIG. 4 is a diagram of a CT scanner according to an embodiment of the application.

FIG. 4 illustrates a schematic diagram of a CT scanner. Scanning preparation parameters are preset since the apparatus for controlling the scanning preparation needs to control the CT scanner to perform the scanning preparation. The first scanning protocol or the second scanning protocol in the above embodiment includes the scanning preparation parameters. The apparatus for controlling the scanning preparation performs the scanning preparation according to the preset scanning preparation parameters.

The scanning preparation parameters may include the following parameters 1-4.

Parameter 1 is a slit of a beam limiting device.

The slit of the beam limiting device for each scanning series is preset.

Parameter 2 is an operation mode of a scanner gantry. The operation mode of the scanner gantry includes a static operation mode and a rotary operation mode.

In a case that the current scanning series is a surview scan, an operation of stopping rotation of the scanner gantry is preset. In a case that the current scanning series is an axial scan or a helical scan, an operation of causing the scanner gantry to rotate at an accelerating rate or at a decelerating rate to reach a required rotation speed is preset.

Parameter 3 is a starting position of the scanner table.

The starting position of the scanner table is preset for each scanning series.

Parameter 4 is an inclination angle of the scanner gantry.

The inclination angle of the scanner gantry is preset for each scanning series.

In the method for controlling the scanning preparation provided by the embodiment of the application, after the first scanning protocol of the current CT examination is obtained, the CT scanner is controlled to perform a scanning preparation for the first scanning series according to the first scanning protocol, instead of performing the scanning preparation after positioning and registration of the object to be scanned as in the conventional technology, therefore, the time for the scanning examination is reduced. Furthermore, for subsequent scanning series, the scanning preparation for the scanning series is performed immediately after completion of exposure of a previous scanning series, therefore, the time for the scanning examination is further reduced. Furthermore, after the last scanning series is completed, a scanning preparation for a first scanning series of a next CT examination is immediately performed, therefore, a time interval between two scanning examinations is made use of and the time for the scanning examination is further reduced.

A set of experimental data is given below, to provide time of CT examinations performed by a CT scanner for a conventional scanning preparation and by a CT scanner for the scanning preparation of the application.

Consider a typical CT examination including a surview scan and a helical scan. Some operating conditions are listed below. Time of CT examinations performed by a CT scanner for the conventional scanning preparation and by a CT scanner for the scanning preparation of the application is listed in the following table, and the time in the following table is in a unit of second. The scanning processes herein satisfy the following conditions 1-3.

In condition 1, the rotation speed of the helical scan is 0.4 second/round, the time for the scanner gantry rotating at 0.4 second/round to stop is 16 seconds, and the time for the scanner gantry in a stationary state to rotate at 0.4 second/round is 16 seconds.

In condition 2, changing of the slit of the beam limiting device, moving of the scanner table, inclining of the scanner gantry and rotating of the scanner gantry may be carried out concurrently, where changing of the rotation speed of the scanner gantry takes a longest time.

In condition 3, a plane film scan is followed by a helical scan in each of the CT examinations.

Referring to table 1 which illustrates the comparison of a CT scanner for the conventional scanning preparation and a CT scanner for the scanning preparation of the application, it takes a significantly reduced time for scanning preparation for a surview scan and for a helical series scan in the application. It can be seen from table 1 that, the total time for the CT examinations taken by the CT scanner for the conventional scanning preparation is about 1.5 time of the total time for the CT examinations taken by the CT scanner for the scanning preparation of the application.

TABLE 1

|   | time for positioning and registration of an object to be scanned | time for scanning preparation for a surview scan | time for a surview scan | time for positioning for a helical series and for parameter modifying | time for scanning preparation for a helical series | time for a helical series scan | total time of CT examinations |
|---|---|---|---|---|---|---|---|
| a CT scanner for the conventional scanning preparation | 20 | 16 | 3 | 20 | 16 | 5 | 80 |
| a CT scanner for the scanning preparation of the application | 20 | 2 | 3 | 20 | 2 | 5 | 52 |

Figure 5:
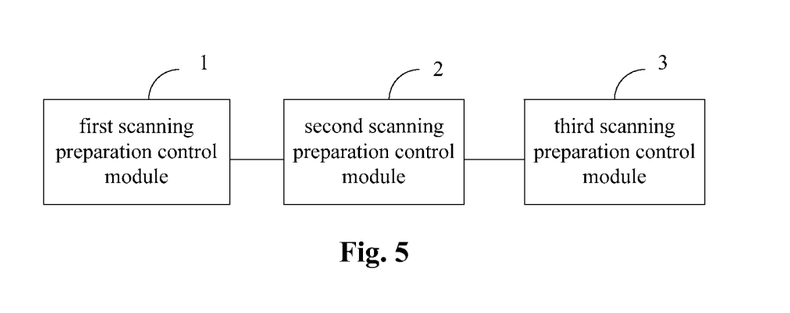
FIG. 5 is a structural diagram of an apparatus for controlling a scanning preparation according to an embodiment of the application.

FIG. 5 illustrates a structural diagram of an apparatus for controlling a scanning preparation according to an embodiment of the application. The apparatus includes a first scanning preparation control module 1, a second scanning preparation control module 2 and a third scanning preparation control module 3.

The first scanning preparation control module 1 is configured to obtain a first scanning protocol of a current CT examination, and control a CT scanner to perform a scanning preparation for a first scanning series according to the first scanning protocol.

The second scanning preparation control module 2 is configured to, in a case that there are one or more subsequent scanning series after the first scanning series, control the CT scanner to perform scanning preparations for the subsequent scanning series according to the first scanning protocol in sequence, where for each of the subsequent scanning series, the scanning preparation for the subsequent scanning series is performed during a time interval between an end of exposure of a scanning series previous to the subsequent scanning series and a starting of the subsequent scanning series.

The third scanning preparation control module 3 is configured to, after completion of a last scanning series, obtain a second scanning protocol of a next CT examination, and control the CT scanner to perform a scanning preparation for a first scanning series according to the second scanning protocol.

In an implementation, the first scanning preparation control module 1 includes: a first scanning protocol obtaining unit, configured to obtain the first scanning protocol of the current CT examination before monitoring that positioning of an object to be scanned is completed, where the first scanning protocol is generated based on registration information of the object to be scanned.

Alternatively, the first scanning preparation control module 1 includes: a first estimated protocol obtaining unit, configured to obtain an estimated first scanning protocol based on detected position information of a scanner table and body information of an object to be scanned after monitoring that positioning of the object to be scanned is completed; a second scanning preparation control unit, configured to control the CT scanner to perform the scanning preparation for the first scanning series according to the estimated first scanning protocol; an actual protocol obtaining unit, configured to obtain an actual first scanning protocol; and a scanning preparation adjusting unit, configured to, in a case that the estimated first scanning protocol is inconsistent with the actual first scanning protocol, obtain a first difference in scanning protocol, where the first difference in scanning protocol is content of the actual first scanning protocol that is different from the estimated first scanning protocol, and control the CT scanner to adjust the scanning preparation for the first scanning series according to the first difference in scanning protocol.

In addition, the apparatus may further include: a positioning completion detection module, configured to determine that the positioning of the object is completed in a case that it is monitored that a weight placed on the scanner table is changed and a door of a CT room is in a closed state in a preset time.

In addition, the apparatus may further include: a first preset information storing module, configured to prestore various pieces of first preset information in a database, where the first preset information includes position information of a scanner table and body information of an object to be scanned, and preset scanning protocols corresponding to the various pieces of the first preset information.

Preferably, the first estimated protocol obtaining unit may include: a first preset information querying subunit, configured to query the database for the first preset information corresponding to the detected position information of the scanner table and body information of the object to be scanned; and a first estimated protocol obtaining subunit, configured to obtain from the database the estimated first scanning protocol corresponding to the obtained first preset information.

In addition, the apparatus may further include: a first scanning protocol updating module, configured to update the first scanning protocol corresponding to the obtained first preset information in the database by using the first difference in scanning protocol.

Preferably, the third scanning preparation control module 3 may include: a second estimated protocol obtaining unit, configured to obtain registration information of a next object to be scanned, and generate an estimated second scanning protocol based on the obtained registration information and estimated positioning information; and a third scanning preparation control unit, configured to control the CT scanner to perform the scanning preparation for the first scanning series according to the estimated second scanning protocol.

In addition, the apparatus may further include: a second preset information storing module, configured to prestore various pieces of second preset information in a database, where the second preset information includes registration information and positioning information of an object to be scanned, and preset scanning protocols of the various pieces of second preset information.

Preferably, the second estimated protocol obtaining unit may include: a second preset information querying subunit, configured to query the database for the second preset information corresponding to the obtained registration information and the estimated positioning information; and a second estimated protocol obtaining subunit, configured to obtain from the database the estimated second scanning protocol corresponding to the obtained second preset information.

In addition, the apparatus may further include: a next actual protocol obtaining module, configured to obtain an actual second scanning protocol after controlling the CT scanner to perform scanning preparation for the first scanning series according to the estimated second scanning protocol; and a next scanning preparation adjusting module, configured to, in a case that the estimated second scanning protocol is inconsistent with the actual second scanning protocol, obtain a second difference in scanning protocol, where the second difference in scanning protocol is content of the actual second scanning protocol that is different from the estimated second scanning protocol, and control the CT scanner to adjust the scanning preparation for the first scanning series according to the second difference in scanning protocol.

In addition, the apparatus may further include: a second scanning protocol updating module, configured to update the second scanning protocol corresponding to the obtained second preset information in the database by using the second difference in scanning protocol.

The first scanning protocol or the second scanning protocol may include scanning preparation parameters, and the scanning preparation parameters may include: a slit of a beam limiting device; an operation mode of a scanner gantry, where the operation mode of the scanner gantry is a static operation mode or a rotation operation mode: a starting position of a scanner table; and an inclination angle of the scanner gantry.

With the method and the apparatus for controlling the scanning preparation of the application, after the first scanning protocol of the current CT examination is obtained, the CT scanner is controlled to perform a scanning preparation for the first scanning series according to the first scanning protocol, instead of performing the scanning preparation after positioning and registration of the object to be scanned as in the conventional technology, therefore, the time for the scanning examination is reduced. Furthermore, for subsequent scanning series, the scanning preparation for the scanning series is performed immediately after completion of exposure of a previous scanning series, therefore, the time for the scanning examination is further reduced. Furthermore, after the last scanning series is completed, a scanning preparation for a first scanning series of a next CT examination is immediately performed, therefore, a time interval between two scanning examinations is made use of and the time for the scanning examination is further reduced.

From the foregoing description of the embodiments, those skilled in the art can clearly understand that all or a few steps of the foregoing methods in the embodiments can be implemented by software and a general hardware platform. Based on the understanding, the essential part of the application or the part contributing to the prior art may be embodied in the form of a software product, and the computer software product may be stored in a storage medium such as a ROM/RAM, a disk, or a CD, etc., including instructions to enable a computing device (may be a personal computer, a server, or a network communication device such as a media gateway, etc.) to execute the embodiments or the methods described in parts of the embodiments.

Since the apparatus disclosed in the embodiments is corresponding to the method disclosed in the method embodiments, the description of the apparatus is simple and related details can be found in the description of the method by reference.

It is to be noted that in the application, the relation terms such as first and second are merely to distinguish one entity or operation from another entity or operation, instead of requiring or implying any actual relationship or order between these entities or operations. Terms "include", "comprise", "contain", or any other variations thereof are intended to cover a non-exclusive inclusion, so that a process, a method, a article or a device including a series of elements includes not only those elements but also other elements that are not explicitly listed out, or further includes inherent elements of the process, a method, a article or a device. Under conditions with no more confinements, the elements limited by a statement "including a . . . " or "comprising a . . . " does not exclude the existence of additional identical elements.

The foregoing description of the disclosed embodiments enables those skilled in the art to implement or use the application. Various modifications of the embodiments are obvious to those skilled in the art, and the general principle defined herein can be implemented in other embodiments without departing from the spirit or scope of the application. Therefore, the application is not limited by the embodiments described herein, but claims a broadest scope that is consistent with the principle and novel features disclosed by the application.

The invention claimed is:

1. A method for controlling a scanning preparation, comprising:
   obtaining a first scanning protocol of a current CT examination, and controlling a CT scanner to perform a scanning preparation for a first scanning series according to the first scanning protocol;
   in a case that there are one or more subsequent scanning series after the first scanning series, controlling the CT scanner to perform scanning preparations for the subsequent scanning series according to the first scanning protocol in sequence, wherein for each of the subsequent scanning series, the scanning preparation for the subsequent scanning series is performed during a time interval between an end of exposure of a scanning series previous to the subsequent scanning series and a starting of the subsequent scanning series; and
   after completion of a last scanning series, obtaining a second scanning protocol of a next CT examination, and controlling the CT scanner to perform a scanning preparation for a first scanning series according to the second scanning protocol.

2. The method according to claim 1, wherein obtaining the first scanning protocol of the current CT examination comprises:
   obtaining the first scanning protocol of the current CT examination before monitoring that positioning of an object to be scanned is completed, wherein the first scanning protocol is generated based on registration information of the object to be scanned.

3. The method according to claim 1, wherein obtaining the first scanning protocol of the current CT examination and controlling the CT scanner to perform the scanning preparation for the first scanning series according to the first scanning protocol comprises:
   obtaining an estimated first scanning protocol based on detected position information of a scanner table and body information of an object to be scanned after monitoring that positioning of the object to be scanned is completed, and controlling the CT scanner to perform the scanning preparation for the first scanning series according to the estimated first scanning protocol;
   obtaining an actual first scanning protocol; and
   in a case that the estimated first scanning protocol is inconsistent with the actual first scanning protocol, obtaining a first difference in scanning protocol, wherein the first difference in scanning protocol is content, which is different from the estimated first scanning protocol, of the actual first scanning protocol, and controlling the CT scanner to adjust the scanning preparation for the first scanning series according to the first difference in scanning protocol.

4. The method according to claim 3, wherein monitoring that the positioning of the object to be scanned is completed comprises:
   determining that the positioning of the object to be scanned is completed in a case that it is monitored that a weight placed on the scanner table is changed and a door of a CT room is in a closed state in a preset time.

5. The method according to claim 3, further comprising:
   prestoring various pieces of first preset information in a database, wherein the first preset information comprises position information of a scanner table and body information of an object to be scanned; and presetting scanning protocols corresponding to the various pieces of the first preset information, and
   obtaining the estimated first scanning protocol based on the detected position information of the scanner table and body information of the object to be scanned comprising:
   querying the database for the first preset information corresponding to the detected position information of the scanner table and body information of the object to be scanned; and
   obtaining from the database the estimated first scanning protocol corresponding to the obtained first preset information.

6. The method according to claim 5, wherein obtaining the second scanning protocol of the next CT examination and controlling the CT scanner to perform the scanning preparation for the first scanning series according to the second scanning protocol comprises:
   obtaining registration information of a next object to be scanned, generating an estimated second scanning protocol based on the obtained registration information and estimated positioning information, and controlling the CT scanner to perform the scanning preparation for the first scanning series according to the estimated second scanning protocol.

7. The method according to claim 6, further comprising:
   prestoring various pieces of second preset information in a database, wherein the second preset information comprises registration information and positioning information of an object to be scanned; and presetting scanning protocols corresponding to the various pieces of the second preset information, and
   generating the estimated second scanning protocol based on the obtained registration information and the estimated positioning information comprising:
   querying the database for the second preset information corresponding to the obtained registration information and the estimated positioning information; and
   obtaining from the database the estimated second scanning protocol corresponding to the obtained second preset information.

8. The method according to claim 7, further comprising:
obtaining an actual second scanning protocol after controlling the CT scanner to perform the scanning preparation for the first scanning series according to the estimated second scanning protocol; and
in a case that the estimated second scanning protocol is inconsistent with the actual second scanning protocol, obtaining a second difference in scanning protocol, wherein the second difference in scanning protocol is content, which is different from the estimated second scanning protocol, of the actual second scanning protocol, and controlling the CT scanner to adjust the scanning preparation for the first scanning series according to the second difference in scanning protocol.

9. The method according to claim 8, further comprising:
updating the first scanning protocol corresponding to the obtained first preset information in the database by using the first difference in scanning protocol; and
updating the second scanning protocol corresponding to the obtained second preset information in the database by using the second difference in scanning protocol.

10. The method according to claim 1, wherein the first scanning protocol or the second scanning protocol comprises scanning preparation parameters, and the scanning preparation parameters comprise:
a slit of a beam limiting device;
an operation mode of a scanner gantry, wherein the operation mode of the scanner gantry is a static operation mode or a rotation operation mode;
a starting position of a scanner table; and
an inclination angle of the scanner gantry.

11. The method according to claim 2, wherein the first scanning protocol or the second scanning protocol comprises scanning preparation parameters, and the scanning preparation parameters comprise:
a slit of a beam limiting device;
an operation mode of a scanner gantry, wherein the operation mode of the scanner gantry is a static operation mode or a rotation operation mode;
a starting position of a scanner table; and
an inclination angle of the scanner gantry.

12. The method according to claim 3, wherein the first scanning protocol or the second scanning protocol comprises scanning preparation parameters, and the scanning preparation parameters comprise:
a slit of a beam limiting device;
an operation mode of a scanner gantry, wherein the operation mode of the scanner gantry is a static operation mode or a rotation operation mode;
a starting position of a scanner table; and
an inclination angle of the scanner gantry.

13. The method according to claim 4, wherein the first scanning protocol or the second scanning protocol comprises scanning preparation parameters, and the scanning preparation parameters comprise:
a slit of a beam limiting device;
an operation mode of a scanner gantry, wherein the operation mode of the scanner gantry is a static operation mode or a rotation operation mode;
a starting position of a scanner table; and
an inclination angle of the scanner gantry.

14. An apparatus for controlling a scanning preparation, comprising:
a first scanning preparation control module, configured to obtain a first scanning protocol of a current CT examination, and control a CT scanner to perform a scanning preparation for a first scanning series according to the first scanning protocol;
a second scanning preparation control module, configured to, in a case that there are one or more subsequent scanning series after the first scanning series, control the CT scanner to perform scanning preparations for the subsequent scanning series according to the first scanning protocol in sequence, wherein for each of the subsequent scanning series, the scanning preparation for the subsequent scanning series is performed during a time interval between an end of exposure of a scanning series previous to the subsequent scanning series and a starting of the subsequent scanning series; and
a third scanning preparation control module, configured to, after completion of a last scanning series, obtain a second scanning protocol of a next CT examination, and control the CT scanner to perform a scanning preparation for a first scanning series according to the second scanning protocol.

15. The apparatus according to claim 14, wherein the first scanning preparation control module comprises:
a first scanning protocol obtaining unit, configured to obtain the first scanning protocol of the current CT examination before monitoring that positioning of an object to be scanned is completed, wherein the first scanning protocol is generated based on registration information of the object to be scanned; and
a first scanning preparation control unit, configured to control the CT scanner to perform the scanning preparation for the first scanning series according to the first scanning protocol.

16. The apparatus according to claim 14, wherein the first scanning preparation control module comprises:
a first estimated protocol obtaining unit, configured to obtain an estimated first scanning protocol based on detected position information of a scanner table and body information of an object to be scanned after monitoring that positioning of the object to be scanned is completed;
a second scanning preparation control unit, configured to control the CT scanner to perform the scanning preparation for the first scanning series according to the estimated first scanning protocol;
an actual protocol obtaining unit, configured to obtain an actual first scanning protocol; and
a scanning preparation adjusting unit, configured to, in a case that the estimated first scanning protocol is inconsistent with the actual first scanning protocol, obtain a first difference in scanning protocol, wherein the first difference in scanning protocol is content, which is different from the estimated first scanning protocol, of the actual first scanning protocol, and control the CT scanner to adjust the scanning preparation for the first scanning series according to the first difference in scanning protocol.

17. The apparatus according to claim 16, further comprising:
a first preset information storing module, configured to prestore various pieces of first preset information in a database, wherein the first preset information comprises position information of a scanner table and body information of an object to be scanned, and preset scanning protocols corresponding to the various pieces of the first preset information, and the first estimated protocol obtaining unit comprising:
a first preset information querying subunit, configured to query the database for the first preset information corresponding to the detected position information of the scanner table and body information of the object to be scanned; and
a first estimated protocol obtaining subunit, configured to obtain from the database the estimated first scanning protocol corresponding to the obtained first preset information.

18. The apparatus according to claim 14, the third scanning preparation control module comprises:
a second estimated protocol obtaining unit, configured to obtain registration information of a next object to be scanned, and generate an estimated second scanning protocol based on the obtained registration information and estimated positioning information; and
a third scanning preparation control unit, configured to control the CT scanner to perform the scanning preparation for the first scanning series according to the estimated second scanning protocol.

19. The apparatus according to claim 18, further comprising:
a second preset information storing module, configured to prestore various pieces of second preset information in a database, wherein the second preset information comprises registration information and positioning information of an object to be scanned, and preset scanning protocols corresponding to the various pieces of the second preset information, and
the second estimated protocol obtaining unit comprising:
a second preset information querying subunit, configured to query the database for the second preset information corresponding to the obtained registration information and the estimated positioning information; and
a second estimated protocol obtaining subunit, configured to obtain from the database the estimated second scanning protocol corresponding to the obtained second preset information.

20. The apparatus according to claim 19, further comprising:
a next actual protocol obtaining module, configured to obtain an actual second scanning protocol after controlling the CT scanner to perform the scanning preparation for the first scanning series according to the estimated second scanning protocol; and
a next scanning preparation adjusting module, configured to, in a case that the estimated second scanning protocol is inconsistent with the actual second scanning protocol, obtain a second difference in scanning protocol, wherein the second difference in scanning protocol is content, which is different from the estimated second scanning protocol, of the actual second scanning protocol, and control the CT scanner to adjust the scanning preparation for the first scanning series according to the second difference in scanning protocol.

\* \* \* \* \*